(12) United States Patent
Wang et al.

(10) Patent No.: US 12,006,424 B2
(45) Date of Patent: Jun. 11, 2024

(54) POLYMER COMPOSITION SUITABLE FOR GAMMA-RAY STERILIZATION

(71) Applicant: BOREALIS AG, Vienna (AT)

(72) Inventors: Jingbo Wang, Linz (AT); Markus Gahleitner, Linz (AT); Klaus Bernreitner, Linz (AT)

(73) Assignee: BOREALIS AG, Vienna (AT)

( * ) Notice: Subject to any disclaimer, the term of this patent is extended or adjusted under 35 U.S.C. 154(b) by 474 days.

(21) Appl. No.: 17/288,668

(22) PCT Filed: Oct. 23, 2019

(86) PCT No.: PCT/EP2019/078794
§ 371 (c)(1),
(2) Date: Apr. 26, 2021

(87) PCT Pub. No.: WO2020/088996
PCT Pub. Date: May 7, 2020

(65) Prior Publication Data
US 2021/0395503 A1    Dec. 23, 2021

(30) Foreign Application Priority Data
Oct. 30, 2018  (EP) .................................... 18203384

(51) Int. Cl.
| | |
|---|---|
| *C08L 23/12* | (2006.01) |
| *A61L 2/08* | (2006.01) |
| *C08K 5/00* | (2006.01) |
| *C08K 5/01* | (2006.01) |
| *C08K 5/1575* | (2006.01) |
| *C08K 5/526* | (2006.01) |

(52) U.S. Cl.
CPC ............... *C08L 23/12* (2013.01); *A61L 2/081* (2013.01); *C08K 5/005* (2013.01); *C08K 5/0083* (2013.01); *C08K 5/01* (2013.01); *C08K 5/1575* (2013.01); *C08K 5/526* (2013.01); *A61L 2202/23* (2013.01); *C08L 2201/08* (2013.01); *C08L 2203/02* (2013.01); *C08L 2314/06* (2013.01)

(58) Field of Classification Search
CPC ............................... C08F 110/06; C08L 23/12
See application file for complete search history.

(56) References Cited

U.S. PATENT DOCUMENTS

2006/0189744 A1    8/2006   Tse et al.

FOREIGN PATENT DOCUMENTS

| CN | 101193970 A | 6/2008 | | |
|---|---|---|---|---|
| CN | 101313026 A | 11/2008 | | |
| EP | 0924251 A1 | 6/1999 | | |
| JP | H06256602 A | 9/1994 | | |
| WO | 2003025047 A1 | 3/2003 | | |
| WO | 2005080495 A1 | 9/2005 | | |
| WO | WO-2016008749 A1 | * | 1/2016 | .............. C08F 2/001 |

OTHER PUBLICATIONS

Applicant: Borealis AG; "A Polymer Composition Suitable for Gamma-Ray Sterilization"; Chinese Patent Application No. 201980070916.5; Chinese First Office Action; dated Jan. 30, 2023; 4 pgs.
Thorat, et al., Gamma-Ray Induced Degradation in Ethylene-Propylene Copolymer, Journal of Applied Polymer Science, 59, 1769-1773.
Busico, Vincenzo, et al., "ALK-1-ENE Polymerization in the Presence of a Monocyclopentadienyl Zirconium(IV) Acetamidinate Catalyst: Microstructural and Mechanistic Insights", Macromol. Rapid Commun. 2007, 28, 1128-1137.
Busico, Vincenzo, et al., "Full Assignment of the 13C NMR Spectra or Regioregular Polypropylenes: Methyl and Methylene Region", Macromolecules 1997, 30, 6251-6263.
Busico, Vincenzo, et al., "Microstructure of Polypropylene", Prog. Polym. Sci. 26 (2001) 443-533.
Cheng, et al., "13C NMR Analysis of Ethylene-Propylene Rubbers", Macromolecules 17, 1984, 1950-1955.
Resconi, Luigi, et al., "Selectivity in Propane Polymerization With Metallocene Catalysts", Chem. Rev. 2000, 100, 1253-1345.
Wang, Wen-Jun, et al., "Structural Analysis of Ethylene/Propylene Copolymers Synthesized With a Constrained Geometry Catalyst", Macromolecules 2000, 33, 1157-1162.
Zhou, Zhe, et al., "A New Decoupling Method for Accurate Quantification of Polyethylene Copolymer Composition and Triad Sequence Distribution With 13C NMR", Journal of Magnetic Resonance 187 (2007) 225-233.
Resconi, et al.; Chemical Reviews, 2000, vol. 100, No. 4; 12 pgs.
Applicant: Borealis AG; "A Polymer Composition Suitable for Gamma-Ray Sterilization"; European Patent Application No. 18203384; Extended European Search Report; dated Apr. 2, 2019; 6 pgs.

* cited by examiner

*Primary Examiner* — Marc S Zimmer
*Assistant Examiner* — Jeffrey S Lenihan
(74) *Attorney, Agent, or Firm* — TAROLLI, SUNDHEIM, COVELL & TUMMINO L.L.P.

(57) ABSTRACT

The present invention is directed to a polymer composition (C) comprising a first propylene homopolymer (H-PP), at least one hydrocarbon oil, at least one nucleating agent and at least one antioxidant, a moulded article formed from said polymer composition, a process for gamma-ray sterilization of said moulded article and uses of hydrocarbon oil in said polymer composition for improving resistance to gamma-ray radiation and reducing discoloration after gamma-ray sterilization in said polymer composition.

13 Claims, No Drawings

POLYMER COMPOSITION SUITABLE FOR GAMMA-RAY STERILIZATION

The present invention is directed to a polymer composition comprising a propylene homopolymer, at least one hydrocarbon oil, at least one nucleating agent, and at least one antioxidant, a moulded article formed from said polymer composition, a process for gamma-ray sterilization of said moulded article and uses of hydrocarbon oil in said polymer composition for improving resistance to gamma-ray radiation and reducing discoloration after gamma-ray sterilization in said polymer composition characterized by a reduced overall migration.

Polypropylene (PP) is one of the most frequently used plastics in packaging applications. In a continuously increasing part of this market, especially in the pharmaceutical area, but also in food packaging and especially in medical applications (syringes, pouches, tubes etc.), the material is sterilized in either heat (steam), radiation (β/electrons or γ) or chemicals (mostly ethylene oxide). However, sterilization processes will inevitably affect the mechanical and optical properties. Due to strong influence of the radiation, sometimes the discoloration becomes visible in the goods.

The application of radiation, especially gamma-ray radiation, induces chain scission and similar degradation effects, resulting in a reduced melt viscosity and severe embrittlement. It has also be found out that these degradation events continue for extended periods of time after the actual sterilization process, making long-term studies necessary for studying the effects.

Thus, there is a need in the art for a polypropylene material featuring an improved resistance to gamma-ray sterilization.

In a first aspect, the present invention is directed to a polymer composition (C), comprising
- (a) 91.0 to 98.0 wt.-% of a propylene homopolymer (H-PP),
- (b) 1.98 to 9.0 wt.-% of at least one hydrocarbon oil (WO),
- (c) 0.01 to 0.7 wt.-% of at least one nucleating agent (NA), and
- (d) 0.01 to 2.0 wt.-% of at least one antioxidant (AO), based on the total weight of the propylene homopolymer (H-PP);

wherein the sum of components (a), (b), (c) and (d) adds up to at least 95 wt.-% of the total weight of the polymer composition (C) and the propylene homopolymer (H-PP) is an isotactic propylene homopolymer defined by
- (i) a melt flow rate $MFR_2$ determined according to ISO1133 at 230° C. and 2.16 kg in the range from 4.0 to 22.0 g/10 min;
- (ii) a melting temperature in the range of 145 to 162° C. as determined by differential scanning calorimetry (DSC); and
- (iii) a content of 2,1 erythro regio-defects in the range from 0.1 to 1.3 mol % as determined by $^{13}$C-NMR spectroscopy.

In a preferred embodiment, the polymer composition (C) has a melt flow rate $MFR_2$ determined according to ISO1133 at 230° C. and 2.16 kg in the range from 5.0 to 25.0 g/10 min, more preferably from 6.0 to 23.0 g/10min.

In another preferred embodiment of the polymer composition (C), the propylene homopolymer (H-PP) has a polydispersity (Mw/Mn) in the range from 2.0 to 4.5 as determined by GPC according to ISO 16014.

In another preferred embodiment of the polymer composition (C), the propylene homopolymer (H-PP) is prepared in the presence of a metallocene catalyst.

In another preferred embodiment of the polymer composition (C), the propylene homopolymer (H-PP) is characterized by a high isotacticity, defined as pentad regularity <mmmm> of more than 96.0 mol % as determined by $^{13}$C-NMR spectroscopy.

In a second aspect, the present invention is directed to a moulded article, preferably an injection moulded article, comprising at least 90 wt.-%, based on the total weight of the moulded article, of the polymer composition (C) according to the first aspect of the invention.

In a preferred embodiment, the moulded article is a medical, pharmaceutical or diagnostic article, preferably selected from the list of articles consisting of catheters, intravenous (IV) sets, laparoscopic instrument components, surgery instrument components, surgical trays, caddies, drug delivery devices, surgical tools, in-vitro diagnostics, tube connectors, tube closures, valves, vials, syringes, plungers, laboratory dishes, and droppers.

In another preferred embodiment, the moulded article has been gamma-ray sterilized at a dose of at least 15 kGy.

In another preferred embodiment, the moulded article has an overall migration in the polymer composition (C) as determined according to EN ISO 1186-14:2002 on injection moulded plaques, 60×60×1 mm$^3$ of less than 60.0 mg/dm$^2$, preferably of less than 55.0 mg/dm$^2$, more preferably less than 50.0 mg/dm$^2$.

In another preferred embodiment, the moulded article has a discoloration of the polymer composition (C) after gamma-ray sterilization at 50 kGy and 60 days of aging as defined by yellowness index of not higher than 23, preferably not higher than 20, and most preferably not higher than 15 as determined on injection moulded plaques 60×60×1 mm$^3$ according to standard method ASTM E313.

In another preferred embodiment, the moulded article is characterized by a Charpy notched impact strength in the range of 2.5 to 15.0 kJ/m$^2$, as determined according to ISO 179 1eA, and a retention of said impact strength after gamma-ray sterilization at 50 kGy and 60 days of aging of more than 75%, preferably of more than 80%, and most preferably of more than 85%.

In a third aspect, the present invention is directed to a process for gamma-ray sterilization of articles comprising the steps of:
providing the moulded article according to the second aspect of the invention, and
subjecting said moulded article to gamma-ray sterilization.

In a preferred embodiment, the gamma-ray sterilization is carried out at a dose in the range of 15 to 150 kGy.

In a fifth aspect, the present invention is directed to the use of a hydrocarbon oil (WO) in the polymer composition (C) according to the first aspect for improving the resistance to gamma-ray radiation of said polymer composition (C). Preferably, said hydrocarbon oil (WO) is a paraffinic oil (white oil) being characterized by a density in the range of 850 to 900 kg/m$^3$ and a viscosity at 20° C. in the range of 50 to 500 mPas.

In a sixth aspect, the present invention is directed to the use of said hydrocarbon oil (WO) in the polymer composition (C) according to the first aspect for reducing discoloration of the polymer composition (C) after gamma-ray sterilization at 50 kGy and 60 days of aging as defined by yellowness index of not higher than 23, preferably not higher than 20, and most preferably not higher than 15 as determined on injection moulded plaques 60×60×1 mm³ according to standard method ASTM E313.

In the following, the present invention is described in more detail.

The Polymer Composition (C)

The inventive polymer composition (C) comprises a propylene homopolymer (H-PP) as the main polymeric component.

Accordingly, the polymer composition (C) preferably comprises, based on the total weight of the polymer composition (C), (a) 91.0 to 98.0 wt.-%, preferably 91.5 to 97.98 wt.-%, more preferably 92.0 to 97.0 wt.-%, even more preferably 93.0 to 96.0 wt.-%, of the propylene homopolymer (H-PP), (b) 1.98 to 9.0 wt.-%, preferably from 2.0 to 8.98 wt.-%, more preferably from 3.0 to 8.0 wt.-%, more preferably from 4.0 to 7.0 wt.-% of at least one paraffinic oil or white oil (WO) having a viscosity at 20° C. in the range of 50 to 500 mPas, (c) 0.01 to 0.70 wt.-%, preferably from 0.02 to 0.60 wt.-%, more preferably from 0.03 to 0.50 wt.-%, of at least one a-nucleating agent (NA), and (d) 0.01 to 2.00 wt.-%, preferably from 0.05 to 1.50 wt.-%, more preferably from 0.10 to 1.00 wt.-% of at least one antioxidant (AO);

The polymer composition (C) may include further additives (AD) in addition to the essential at least one nucleating agent (NA) and/or at least one antioxidant (AO).

Preferably, the polymer composition (C) does not comprise further polymeric materials different to the propylene homopolymer (H-PP) in an amount exceeding 5.0 wt.-%, preferably in an amount exceeding 3.0 wt.-%, more preferably in an amount exceeding 2.5 wt.-%, based on the total weight of the polymer composition (C).

Further, the sum of components (a), (b), (c) and (d) adds up to at least 95 wt.-% of the total weight of the polymer composition (C) while it is preferred that the polymeric material of the polymer composition (C) consists of the propylene homopolymer (H-PP), the at least one paraffinic or white oil (WO) having a dynamic viscosity at 20° C. according to ASTM D 445 in the range from 50 to 500 mPas, the at least one nucleating agent (NA), and the at least one antioxidant (AO).

The polymer composition (C) preferably has a melt flow rate $MFR_2$ (230° C., 2.16 kg) determined according to ISO 1133 in the range of 5.0 to 25.0 g/10 min, more preferably in the range of 6.0 to 23.0 g/10 min, even more preferably in the range of 7.0 to 20.0 g/10 min.

Further, the polymer composition (C) preferably has a melting temperature measured by differential scanning calorimetry (DSC) according to ISO 11357 in the range of 145 to 162° C., more preferably in the range of 148 to 161° C., still more preferably in the range of 150 to 160° C.

Further, the polymer composition (C) preferably has a crystallization temperature measured by differential scanning calorimetry (DSC) according to ISO 11357 in the range of 115 to 129° C., more preferably in the range of 118 to 127° C., still more preferably in the range of 120 to 126° C.

The polymer composition (C) preferably has a xylene soluble (XCS) content of below 7.0 wt.-%, preferably from 1.5 to 6.5 wt.-%, more preferably from 1.8 to 6.0 wt.-%.

The polymer composition (C) preferably has flexural modulus as determined according to ISO 178 in the range from 900 to 1350 MPa, more preferably from 950 to 1300 MPa, and even more preferably from 1225 to 1275 MPa.

The Propylene Homopolymer (H-PP)

The propylene homopolymer (H-PP) is the major component of the polymer composition (C) of the present invention.

According to the present invention, the expression "propylene homopolymer", as used for the first homopolymer (H-PP), relates to a polypropylene that consists substantially, i.e. of at least 99.4 mol-%, more preferably of at least 99.6 mol-%, still more preferably of at least 99.7 mol-%, like of at least 99.9 mol-%, of propylene units. In another embodiment only propylene units are detectable, i.e. only propylene has been polymerized. The definition "propylene homopolymer" has a well-known meaning in the art.

The propylene homopolymer (H-PP) is preferably obtained by polymerization with a metallocene catalyst. This is important because polypropylenes prepared by using an isospecific, C2-symmetric metallocene provide a different microstructure compared to polypropylenes prepared by using Ziegler-Natta (ZN) catalysts. The most significant difference is the presence of regio-defects in metallocene-made polypropylenes. These regio-defects can be of three different types, namely 2,1-erythro (2,1e), 2,1-threo (2,1t) and 3,1 defects. A detailed description of the structure and mechanism of formation of regio-defects in polypropylene can be found in Chemical Reviews 2000, 100(4), pages 1316-1327.

Accordingly, the term "regio defects" herein defines the sum of 2,1 erythro regio-defects, 2,1 threo regio-defects and 3,1 regio-defects. Consequently, the amount of defects, i.e. regio defects, like 2,1 regio defects, i.e. 2,1 erythro regio-defects and 2,1 threo regio-defects, and 3,1 regio-defects, is indicated by "mol %" of the average percentage of propylene units in the polymer chain.

In another preferred embodiment, the propylene homopolymer (H-PP) has a sum of 2,1 erythro regio-defects, 2,1 threo regio-defects and 3,1 regio-defects from 0.1 to 1.3 mol %, preferably from 0.2 to 1.1 mol %, even more preferably from 0.2 to 1.0 mol %, and most preferably from 0.3 to 0.8 mol %, as determined by $^{13}$C-NMR spectroscopy.

The presence of such amount of regio-defects is a sufficient (although not a mandatory) feature to unambiguously identify a polypropylene as produced with a metallocene catalyst instead of a Ziegler-Natta-type catalyst.

In another preferred embodiment, the propylene homopolymer (H-PP) is characterized by a high isotacticity, defined as pentad regularity <mmmm>of more than 96.0 mol %, preferably of more than 96.5 mol %, most preferably of 97.0 mol %, as determined by $^{13}$C-NMR spectroscopy.

It is preferred that the propylene homopolymer (H-PP) has a melt flow rate $MFR_2$ (230° C., 2.16 kg) determined according to ISO 1133 in the range from 4.0 to 22.0 g/10 min, preferably in the range of 5.0 to 20.0 g/10 min, still more preferably in the range of 6.0 to 18.0 g/10 min It is further preferred that the propylene homopolymer (H-PP) is featured by rather low cold xylene solubles (XCS) content, i.e. by a xylene cold solubles (XCS) below 6.0 wt.-%. Accordingly, the propylene homopolymer (H-PP), has preferably a xylene cold solubles (XCS) content in the range of 0.5 to 7.0 wt.-%, more preferably in the range of 1.5 to 6.0 wt.-%, still more preferably in the range of 2.5 to 5.0 wt.-%.

The amount of xylene cold solubles (XCS) additionally indicates that the propylene homopolymer is preferably free of any elastomeric polymer component, like an ethylene propylene rubber. In other words, the propylene homopolymer (H-PP) is preferably not a heterophasic polypropylene, i.e. a system consisting of a polypropylene matrix in which an elastomeric phase is dispersed. Such systems are featured by a rather high xylene cold soluble content. In other words, the propylene homopolymer (H-PP) is a monophasic polypropylene.

Further, the propylene homopolymer (H-PP) is preferably a crystalline propylene homopolymer. The term "crystalline" indicates that the propylene homopolymer (H-PP) has a relatively high melting temperature. In particular it is preferred that the propylene homopolymer (H-PP) has a melting temperature Tm in the range from 145 to 162° C., preferably in the range from 148 to 161° C., more preferably in the range from 150 to 160° C. as measured by differential scanning calorimetry (DSC) according to ISO 11357.

In another preferred embodiment, the propylene homopolymer (H-PP) has a polydispersity (Mw/Mn) in the range from 2.0 to 4.5, more preferably from 2.5 to 4.2, and even more preferably from 2.8 to 4.0, as determined by GPC according to ISO 16014.

The propylene homopolymer (H-PP) may contain suitable additives as known in the art. According to this invention, the additives of the propylene homopolymer (H-PP) are regarded being part of the "additives (AD)" as described in more detail in the below section "The Additives".

The Hydrocarbon Oil (WO)

The hydrocarbon oil, preferably the paraffinic oil or white oil (WO) is another essential component of the polymer composition (C) of the present invention.

The term "paraffinic oil" or "white oil" as used in the present invention refers to a highly refined mineral oil that is very pure, stable, colorless, odorless, non-toxic and chemically inert. White oil is a liquid mixture of hydrocarbons obtained from petroleum by treatment with sulfuric acid and oleum or by hydrogenation or a combination thereof White oil predominantly contains or essentially consists of a mixture of C15 to C50 saturated hydrocarbons. The white oil (WO) can be produced from a variety of petroleum feedstocks. White oil is a colorless transparent oily liquid, insolvent in water, and soluble in benzene, chloroform, ether, petrol, ether, carbon disulfide, and volatile oils. Liquids typically known and marketed as paraffin oils (CAS 8012-95-1), like known under the term nujol, or silicon oils also are generally considered white oils in the sense of the present invention. One especially preferred white oil (WO) is commercially available as Primol 352 (ExxonMobil).

The term "white oil (WO)" preferably includes pharmaceutical grade mineral oils meeting the requirements of USP 23 and relevant FDA regulations provided in e.g. 37 CFR 172.878 and 178.3620(a). Technical grade mineral oils meeting the FDA regulation provided in 178.3620(b) are not suitable for the present invention or at least generally less preferred.

White oil (WO) according to the present invention preferably has a relative density at 20° C. as measured by ASTM D 4052 in the range from 850 to 900 kg/m$^3$, more preferably in the range from 855 to 890 kg/m$^3$, even more preferably in the range from 857 to 880 kg/m$^3$.

The white oil (WO) according to the present invention preferably has a dynamic viscosity at 20° C. according to ASTM D 445 in the range from 50 to 500 mPas, more preferably from 60 to 400 mPas, even more preferably from 70 to 300 mPas.

Further, it is preferred that the white oil (WO) according to the present invention has a pour point as determined by ASTM D 5950 of below 0° C., preferably in the range from −50° C. to −5° C., more preferably from −40° C. to −10° C.

The Nucleating Agent (NA)

The polymer composition (C) according to the present invention preferably comprises at least one nucleating agent (NU), preferably an α-nucleating agent.

The term "α-nucleating agent" denotes at least one compound, which is added to increase the crystallization rate of a polymer resulting in an increased degree of crystallinity and usually a smaller crystal size. The nucleating can be soluble or particular, wherein soluble nucleating agents (or "clarifiers" or "clarifying agents") are preferred.

The at least one α-nucleating agent (NU) when being soluble nucleating agent preferably has the following structure,

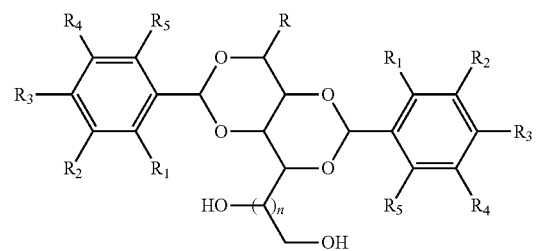

wherein R is independently selected from the group consisting of hydrogen, alkyl, alkenyl, alkynyl, alkoxy, aryloxy, hydroxyalkyl, alkyl halide cycloalkyl, cycloalkenyl, aryl, substituted aryl, and combinations thereof, and wherein $R_1$ to $R_5$ are independently selected from the group consisting of hydrogen, alkyl, alkenyl, alkynyl, alkoxy, aryloxy, hydroxyalkyl, cycloalkyl, cycloalkenyl, aryl, substituted aryl, halide, amino and thioether and combinations thereof, and optionally any adjacent $R_1$ to $R_5$ are linked together to form a 5-membered or 6-membered ring, and wherein n is an integer from 0 to 2, preferably an integer from 1 to 2, more preferably n is 1.

Preferably, R is selected from the group consisting of hydrogen, methyl, ethyl, iso-propyl, n-butyl, sec-butyl, iso-butyl and tert-butyl, and $R_1$ to $R_5$ are independently selected from the group consisting of hydrogen, chlorine, methyl, ethyl, n-propyl, iso-propyl, n-butyl, sec-butyl, iso-butyl and tert-butyl, and n is 1.

Still more preferably, R is hydrogen and $R_1$ to $R_5$ are independently selected from the group consisting of hydrogen, chlorine, methyl, ethyl, n-propyl, iso-propyl, n-butyl, sec-butyl, iso-butyl and tert-butyl, and n is 1.

Yet more preferably, R is hydrogen and $R_1$ to $R_5$ are independently selected from the group consisting of hydrogen, chlorine, methyl, ethyl, and tert-butyl, and n is 1.

It should be noted that although only the 1,3:2,4 isomer is represented, this structure is provided for convenience and illustration only and this definition is not limited to only isomers of the 1,3:2,4 type, but includes any other isomers, such as the 3,5:4,6 type or the 2,4:3,5 type.

Even more preferably the at least one nucleating agent (NU) is selected from the group consisting of 1,3:2,4 bis (dibenzylidene)sorbitol, 1,3:2,4 bis(4-methylbenzylidene) sorbitol, 1,3:2,4 bis(4-ethylbenzylidene)sorbitol, 1,3:2,4 bis (3,4-dimethylbenzylidene)sorbitol, and 1,3:2,4 bis(3-chlorobenzylidene) sorbitol.

Yet even more preferably the at least one nucleating agent (NU) comprises 1,3:2,4 bis(3,4-dimethylbenzylidene)sorbitol.

According to a preferred embodiment, the at least one nucleating agent (NU) in the polymer composition (C) consists of one or more nucleating agents according to the structure depicted above.

The polymer composition (C) preferably comprises the at least one nucleating agent (NU) in an amount from 0.01 to 0.70 wt.-%, preferably from 0.02 to 0.60 wt.-%, more preferably from 0.03 to 0.50 wt.-%, based on the total weight of the polymer composition.

In another preferred embodiment, the at least one nucleating agent (NU) may alternatively or additionally, comprise a compound selected from the group consisting of salts of monocarboxylic acids and polycarboxylic acids, for example sodium benzoate, phosphorous-based compounds, for instance mono-, bis- or tetraphenyl phosphates, for example sodium 2,2'-methylene bis-(4,6-di-tert-butylphenyl) phosphate or hydroxybis (2,4,8,10-tetra-tert-butyl-6-hydroxy-12H-dibenzo(d,g)(1,3,2) dioxaphosphocin 6-oxidato) aluminium, or any mixtures, as well as polymeric nucleating agents.

In one preferred embodiment, the at least one nucleating agent (NU) comprises a polymeric nucleating agent, more preferably a polymer of vinyl compound, in particular a polymeric nucleating agent obtainable by polymerising vinylcycloalkane monomers or vinylalkane monomers.

The polymeric nucleating agent is preferably a polymerized vinyl compound according to the following formula

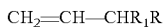

wherein $R_1$ and $R_2$ together form a 5- or 6-membered saturated, unsaturated or aromatic ring, optionally containing substituents, or independently represent an alkyl group comprising 1 to 4 carbon atoms, whereby in case $R_1$ and $R_2$ form an aromatic ring, the hydrogen atom of the —$CHR_1R_2$ moiety is not present.

Even more preferably, the polymeric nucleating agent is selected from vinyl cycloalkane polymer, in particular vinyl cyclohexane (VCH) polymer, vinyl cyclopentane polymer, 3-methyl-1-butene polymer and vinyl-2-methyl cyclohexane polymer. One very preferred polymeric nucleating agent includes as the at least one nucleating agent (NU) vinyl cyclohexane (VCH) polymer.

The at least one nucleating agent (NU) may be introduced to the polymer composition during the polymerisation process of the propylene homopolymer (h-PP) or at a later stage, for example by a post polymerization processes, including admixing the at least one nucleating agent (NU) using the master batch technology.

If a polymeric nucleating agent is used, like vinyl cyclohexane (VCH) polymer, it is preferred to introduce the polymeric nucleating agent into the polymer compositing during the polymerisation process of the polypropylene (PP). It is further appreciated that the propylene homopolymer (H-PP) and optionally the polymeric nucleating agent are the only polymers present in the polymer composition.

As indicated above, the polypropylene composition may comprise additional nucleating agents such as talc. However, according to a preferred embodiment, the at least one nucleating agent (NU) consists of alpha nucleating agents exclusively, while beta nucleating agents are not present in the polymer composition.

The Antioxidant (AO)

The polymer composition (C) comprises at least one antioxidant (AO) as another essential component.

The term "antioxidant (AO)" as used herein includes primary and secondary antioxidants.

Primary antioxidants act as radical scavengers in the oxidation cycle. Primary antioxidants stabilize polypropylene material by scavenging radicals formed in a polypropylene thereby interrupting the oxidation cycle that slows leads to the degradation of the polypropylene over time. The auto-oxidation cycle in polypropylenes is basically a free-radical initiated chain reaction, which can be inhibited by the presence of radical scavengers. Primary antioxidants includes the class of hindered phenols and hindered amines.

Hindered phenols are sterically hindered phenols, which act as H-donors by forming a phenoxyl radical that is stabilized by steric hindrance of bulky substitutents in the 2,6-position. However, it is preferred that the polymer composition (C) of the present invention includes at least one antioxidant (AO) with the proviso that the antioxidant is not a hindered phenol compound or, alternatively, the antioxidant is not a hindered phenol compound and not a hindered amine. The presence of a hindered phenol compound in a polypropylene subjected to gamma-ray sterilization leads to the degradation of the hindered phenol and the build-up of colored degradation products which negatively affect the optical properties of the polypropylene composition.

In other words, the antioxidant of the present invention is preferably a hindered amine compound. This class of compounds is also sometimes referred to as hindered amine light stabilizers (HALS). Hindered amine compounds are preferably secondary aromatic amines, which scavenge radicals through a nitroxyl radical formed from the hindered amine.

Secondary antioxidants, which also belong to the antioxidants (AO) of the present invention, do not primarily act by scavenging radicals but show a synergistic effect when combined with primary antioxidants. Preferred secondary antioxidants (AO) are phosphites and thio compounds, like thioesters.

The polymer composition (C) preferably comprises the at least one antioxidant (AO) in an amount from 0.01 wt.-% to 2.00 wt.-%, more preferably in the range from 0.05 to 1.00 wt.-%, even more preferably in the range from 0.10 to 0.75 wt.-%, or in the range from 0.20 to 0.50 wt.-%, and most preferably in the range from 0.35 to 0.40 wt.-%, based on the total weight of the propylene homopolymer (H-PP).

The Additives (AD)

In one embodiment, the polymer composition (C) may further include additives (AD). The additives (AD) may be added separately to the polymer composition (C) and/or are introduced as part of the propylene homopolymer (H-PP).

The amount of additives (AD in the polymer composition (C) is from 0.0 to 5.0 wt.-%, more preferably 0.05 to 4.0 wt.-%, still more preferably 0.1 to 3.0 wt.-% of additives (AD), based on the total weight of the polymer composition (C).

In the polymer composition (C) according to the present invention, at least one nucleating agent (NA) and/or at least one antioxidant (AO) are considered essential components. Accordingly, the at least one nucleating agent and at least one antioxidant (AO) are not considered additives (AD) as separately defined herein.

Rather, typical additives (AD) according to this definition include acid scavengers, like calcium stearate, colorants, light stabilisers or UV stabilizers, plasticizers, slip agents, anti-scratch agents, dispersing agents, processing aids, lubricants, pigments, fillers, and the like. Especially preferred in the polymer composition (C) is the presence of at least one light stabilizer, in addition to the at least one antioxidant and the at least one nucleating agent.

Suitable additives are commercially available and for example described in "Plastic Additives Handbook", 6th edition 2009 of Hans Zweifel (pages 1141 to 1190).

Furthermore, the term "additives (AD)" according to the present invention may also include any carrier materials, for instance polymeric carrier materials, like polymeric carrier material(s) present in optional masterbatch (MB) of an additive (AD). Accordingly the carrier material, like the polymeric carrier material, is part of the additives (AD) and not considered as a "polymeric material" as defined above.

Therefore any additional polymer being a carrier material for additives (AD) is not calculated to the amount of propylene homopolymer (H-PP) as indicated in the present invention, but to the amount of the respective additive (AD).

The Moulded Article

In another aspect, the present invention is directed to a moulded article comprising the polymer composition (C) comprising the propylene homopolymer (H-PP).

The moulded article of the present invention preferably comprises at least 90 wt.-%, more preferably at least 95 wt.-%, yet more preferably at least 98 wt.-% of the polymer composition (C), based on the total weight of the moulded article. Even more preferably, the moulded article consists of the polymer composition (C) as defined above.

The moulded article according to the present invention is preferably an injection moulded article. With respect to the field of application of the moulded article and its preferred use, the moulded article preferably is a medical, pharmaceutical or diagnostic article.

With respect to its use in the medical or pharmaceutical field or its use for diagnostic applications, the moulded article according to the present invention is preferably selected from the list of moulded articles consisting of catheters, intravenous infusion sets, laparoscopic instrument components, surgery instrument components, surgical trays, caddies, drug delivery devices, surgical tools, in-vitro diagnostics, tube connectors, tube closures, valves, vials, syringes, plungers, laboratory dishes, and droppers.

Preferably, the moulded article has been gamma-ray sterilized at a dose of at least 5 kGy, like at least 15 kGy, or more preferably with a dose of gamma-ray radiation from 15 to 150 kGy, even more preferably from 25 to 100 kGy, or most preferably from 30 to 60 kGy.

In another embodiment, the moulded article has an overall migration in the polymer composition (C) as determined according to EN ISO 1186-14:2002 on injection moulded plaques, 60×60×1 mm$^3$ of less than 80.0 mg/dm$^2$, preferably of less than 70.0 mg/dm$^2$, more preferably less than 60.0 mg/dm$^2$ and even more preferably less than 50.0 mg/dm$^2$, and/or the moulded article has a degree of discoloration of the polymer composition (C) after gamma-ray sterilization at 50 kGy and 60 days of aging as defined by yellowness index (YI) of not higher than 23, preferably not higher than 20, and most preferably not higher than 15 as determined on injection moulded plaques 60×60×1 mm$^3$ according to standard method ASTM E313.

In another preferred embodiment, the moulded article according to the present invention is characterized by a Charpy notched impact strength in the range of 2.5 to 15.0 kJ/m$^2$, preferably in the range of 2.8 to 12.0 kJ/m$^2$ as determined according to ISO 179 1eA, and a retention of said impact strength after gamma-ray sterilization at 50 kGy and 60 days of aging of more than 75%, preferably of more than 80%, and most preferably of more than 85%.

In another aspect, the present invention is directed to a process for gamma-ray sterilization of the moulded article as herein defined comprising the steps of:
 providing the moulded article of the present invention, and
 subjecting said moulded article to gamma-ray sterilization.

Preferably, in said process, gamma-ray sterilization is carried out at a dose of at least 15 kGy.

In another aspect, the present invention is directed to the following three uses:

The use of paraffinic oil or white oil (WO) in the polymer composition (C) according to the present invention for reducing the level of overall migration in said polymer composition (C) as determined according to EN ISO 1186-14:2002 on injection moulded plaques, 60×60×1 mm$^3$ to less than 60.0 mg/dm$^2$, preferably of less than 55.0 mg/dm$^2$, more preferably less than 50.0 mg/dm$^2$.

The use of white oil (WO) in the polymer composition (C) according to the present invention for improving the resistance to gamma-ray radiation of said polymer composition (C).

The use of white oil (WO) in the polymer composition (C) according to the present invention for reducing discoloration of said polymer composition (C) after gamma-ray sterilization at 50kGy and 60 days of aging as defined by yellowness index (YI) of not higher than 23, preferably not higher than 20, and most preferably not higher than 15 as determined on injection moulded plaques 60×60×1 mm$^3$ according to standard method ASTM E313.

The present invention will be described in further detail by the examples provided below.

EXAMPLES

A. Measuring Methods

The following definitions of terms and determination methods apply for the above general description of the invention as well as to the below examples unless otherwise defined.

MFR$_2$ (230° C.) is measured according to ISO 1133 (230° C., 2.16 kg load).

Quantification of Microstructure by NMR Spectroscopy

Quantitative nuclear-magnetic resonance (NMR) spectroscopy was used to quantify the comonomer content and comonomer sequence distribution of the polymers. Quantitative $^{13}$C {$^{1}$H} NMR spectra were recorded in the solution-state using a Bruker Advance III 400 NMR spectrometer operating at 400.15 and 100.62 MHz for $^{1}$H and $^{13}$C respectively. All spectra were recorded using a $^{13}$C optimised 10 mm extended temperature probehead at 125° C. using nitrogen gas for all pneumatics. Approximately 200 mg of material was dissolved in 3 ml of 1,2-tetrachloroethane-d$_2$ (TCE-d2) along with chromium-(III)-acetylacetonate (Cr(acac)$_3$) resulting in a 65 mM solution of relaxation agent in solvent (Singh, G., Kothari, A., Gupta, V., Polymer Testing 28 5 (2009), 475). To ensure a homogenous solution, after initial sample preparation in a heat block, the NMR tube was further heated in a rotatary oven for at least 1 hour. Upon insertion into the magnet the tube was spun at 10 Hz. This setup was chosen primarily for the high resolution and quantitatively needed for accurate ethylene content quantification. Standard single-pulse excitation was employed without NOE, using an optimised tip angle, 1 s recycle delay and a bi-level WALTZ16 decoupling scheme (Zhou, Z., Kuemmerle, R., Qiu, X., Redwine, D., Cong, R., Taha, A., Baugh, D. Winniford, B., J. Mag. Reson. 187 (2007) 225; Busico, V., Carbonniere, P., Cipullo, R., Pellecchia, R., Severn, J., Talarico, G., Macromol. Rapid Commun. 2007, 28, 1128). A total of 6144 (6k) transients were acquired per spectra. Quantitative $^{13}$C {$^{1}$H} NMR spectra were processed, integrated and relevant quantitative properties determined from the integrals using proprietary computer programs. All chemical shifts were indirectly referenced to the central methylene group of the ethylene block (EEE) at 30.00 ppm using the chemical shift of the solvent. This approach allowed comparable referencing even when this structural unit was not present. Characteristic signals corresponding to the incorporation of ethylene were observed Cheng, H. N., Macromolecules 17 (1984), 1950).

For polypropylene homopolymers all chemical shifts are internally referenced to the methyl isotactic pentad (mmmm) at 21.85 ppm.

Characteristic signals corresponding to regio defects (Resconi, L., Cavallo, L., Fait, A., Piemontesi, F., Chem. Rev. 2000, 100, 1253; Wang, W-J., Zhu, S., Macromolecules 33 (2000), 1157; Cheng, H. N., Macromolecules 17 (1984), 1950) or comonomer were observed.

The tacticity distribution was quantified through integration of the methyl region between 23.6-19.7 ppm correcting for any sites not related to the stereo sequences of interest (Busico, V., Cipullo, R., Prog. Polym. Sci. 26 (2001) 443; Busico, V., Cipullo, R., Monaco, G., Vacatello, M., Segre, A. L., Macromoleucles 30 (1997) 6251).

Specifically the influence of regio defects and comonomer on the quantification of the tacticity distribution was corrected for by subtraction of representative regio defect and comonomer integrals from the specific integral regions of the stereo sequences.

The isotacticity was determined at the pentad level and reported as the percentage of isotactic pentad (mmmm) sequences with respect to all pentad sequences:

[mmmm] %=100*(mmmm/sum of all pentads)

The presence of 2,1 erythro regio defects was indicated by the presence of the two methyl sites at 17.7 and 17.2 ppm and confirmed by other characteristic sites.

Characteristic signals corresponding to other types of regio defects were not observed (Resconi, L., Cavallo, L., Fait, A., Piemontesi, F., Chem. Rev. 2000, 100, 1253).

The amount of 2,1 erythro regio defects was quantified using the average integral of the two characteristic methyl sites at 17.7 and 17.2 ppm:

$P_{21e} = (I_{e6} + I_{e8})/2$

The amount of 1,2 primary inserted propene was quantified based on the methyl region with correction undertaken for sites included in this region not related to primary insertion and for primary insertion sites excluded from this region:

$P_{12} = I_{CH3} + P_{12}e$

The total amount of propene was quantified as the sum of primary inserted propene and all other present regio defects:

$P_{total} = P_{12} + P_{21}e$

The mole percent of 2,1 erythro regio defects was quantified with respect to all propene:

$[21e]\ mol\% = 100*(P_{21e}/P_{total})$

For copolymers characteristic signals corresponding to the incorporation of ethylene were observed (Cheng, H. N., Macromolecules 17 (1984), 1950).

With regio defects also observed (Resconi, L., Cavallo, L., Fait, A., Piemontesi, F., Chem.

Rev. 2000, 100, 1253; Wang, W -J., Zhu, S., Macromolecules 33 (2000), 1157; Cheng, H. N., Macromolecules 17 (1984), 1950) correction for the influence of such defects on the comonomer content was required.

Number Average Molecular Weight (Me), Weight Average Molecular Weight (Mw) and Molecular Weight Distribution (MWD)

Molecular weight averages (Mw, Mn), and the molecular weight distribution (MWD), i.e. the Mw/Mn (wherein Mn is the number average molecular weight and Mw is the weight average molecular weight), were determined by Gel Permeation Chromatography (GPC) according to ISO 16014-4:2003 and ASTM D 6474-99. A PolymerChar GPC instrument, equipped with infrared (IR) detector was used with 3× Olexis and 1x Olexis Guard columns from Polymer Laboratories and 1,2,4-trichlorobenzene (TCB, stabilized with 250 mg/L 2,6-Di tert butyl-4-methyl-phenol) as solvent at 160° C. and at a constant flow rate of 1 mL/min 200 µL of sample solution were injected per analysis. The column set was calibrated using universal calibration (according to ISO 16014-2:2003) with at least 15 narrow MWD polystyrene (PS) standards in the range of 0.5 kg/mol to 11 500 kg/mol. Mark Houwink constants for PS, PE and PP used are as described per ASTM D 6474-99. All samples were prepared by dissolving 5.0-9.0 mg of polymer in 8 mL (at 160° C.) of stabilized TCB (same as mobile phase) for 2.5 hours for PP or 3 hours for PE at max. 160° C. under continuous gentle shaking in the autosampler of the GPC instrument. DSC analysis, melting temperature ($T_m$) and melting enthalpy (H.), crystallization temperature ($T_e$) and crystallization enthalpy (He): measured with a TA Instrument Q200 differential scanning calorimetry (DSC) on 5 to 7 mg samples. DSC is run according to ISO 3146/part 3/method C2 in a heat/cool/heat cycle with a scan rate of 10° C./min in the temperature range of −30 to +225° C. Crystallization temperature ($T_c$) and crystallization enthalpy ($H_c$) are determined from the cooling step, while melting temperature ($T_m$) and melting enthalpy ($H_m$) are determined from the second heating step.

Density of the polymer is measured according to ISO 1183-187. Sample preparation is done by compression moulding in accordance with ISO 1872-2:2007. Density of the hydrocarbon oil is determined according to ASTM D 4052 at 15° C.

The xylene solubles (XCS, wt.-%): Content of xylene cold solubles (XCS) is determined at 25° C. according ISO 16152; first edition; 2005-07-01. The part which remains insoluble is the xylene cold insoluble (XCI) fraction.

Flexural Modulus: The flexural modulus was determined in 3-point-bending according to ISO 178 on injection molded specimens of 80×10×4 mm prepared in accordance with ISO 294-1:1996.

Impact: Charpy notched impact strength is determined according to ISO 179/1 eA at 23° C. by using injection moulded test specimens as described in EN ISO 1873-2 (80×10×4 mm).

Haze was determined according to ASTM D1003-00 on 60×60×1 mm³ plaques injection molded in line with EN ISO 1873-2 using a melt temperature of 200° C. and on cast films of 50 µm thickness produced on a monolayer cast film line with a melt temperature of 220° C. and a chill roll temperature of 20° C.

B-Viscosity was determined according to ASTM D 3236 at 190° C.

Overall Migration

Overall Migration is determined according to EN ISO 1186-14:2002 on injection moulded plaques, 60×60×1 mm³.

Irradiation

Injection moulded test specimen of 80×10×4 mm³ for Charpy or 60×60×1 mm³ for

Yellowness Index, both prepared in accordance with EN ISO 1873-2, were exposed to gamma-ray irradiation at 50 kGy using a 60Co γ-ray source. Consecutively the samples were aged at 80° C. in a circulating air oven up to 60 days as indicated below. Once the desired time was reached, the samples were taken out from the oven and aged at 23° C. for 24 hours before the impact test according to Charpy ISO 179/1eA+23° C. was performed.

Parallel to the irradiated samples, according non-irradiated samples were aged at 80° C. in a circulating air oven up to 60 days.

B. Examples

1. The First Propylene Homopolymer (H-PP1):

The first propylene homopolymer (H-PP1) was prepared by polymerization using a metallocene catalyst as described in detail in WO 2015/011135 A1 (metallocene complex MC1 with methylaluminoxane (MAO) and borate resulting in Catalyst 3 described in WO 2015/011135 A1) with the proviso that the surfactant is 2,3,3,3-tetrafluoro-2-(1,1,2,2,3,3,3-heptafluoropropoxy)-1-propanol. The metallocene complex (MC1 in WO 2015/011135 A1) is prepared as described in WO 2013/007650 A1 (metallocene E2 in WO 2013/007650 A1).

Off-Line Prepolymerization Procedure

The catalyst used in the polymerization process was prepared as follows:

The metallocene (MC1) (rac-anti-dimethylsilandiyl(2-methyl-4-phenyl-5-methoxy-6-tert-butyl-indenyl)(2-methyl-4-(4-tert-butylphenyl)indenyl)zirconium dichloride) has been synthesized as described in WO 2013/007650.

The catalyst was prepared using metallocene MC1 and a catalyst system of MAO and trityl tetrakis(pentafluorophenyl)borate according to Catalyst 3 of WO 2015/11135 with the proviso that the surfactant is 2,3,3,3-tetrafluoro-2-(1,1,2,2,3,3,3-heptafluoropropoxy)-1-propanol.

The catalyst MC-1 was pre-polymerized according to the following procedure: Off-line pre-polymerization experiment was done in a 125 mL pressure reactor equipped with gas-feeding lines and an overhead stirrer. Dry and degassed perfluoro-1.3-dimethylcyclohexane (15 cm$^3$) and the desired amount of the catalyst to be pre-polymerized were loaded into the reactor inside a glove box and the reactor was sealed. The reactor was then taken out from the glove box and placed inside a water cooled bath kept at 20° C. The overhead stirrer and the feeding lines were connected and stirring speed set to 450 rpm. The experiment was started by opening the propylene feed into the reactor. The total pressure in the reactor was raised to about 5 barg and held constant by propylene feed via mass flow controller until the target degree of polymerization was reached (10 min). The reaction was stopped by flashing the volatile components. Inside glove box, the reactor was opened and the content poured into a glass vessel. The perfluoro-1,3-dimethylcyclohexane was evaporated until a constant weight was obtained to yield the pre-polymerized catalyst.

TABLE 1

Off-line prepolymerization

| Metallocene | Catalyst amount [mg] | Prepolymerization Degree [wt %/wt %] |
|---|---|---|
| MC-1 | 104 | 3.19 |

TABLE 2

Preparation of propylene homopolymer (H-PP1) and final properties

| | | H-PP1 |
|---|---|---|
| Prepolymerization | | |
| Temperature | ° C. | 20 |
| Pressure | kPa | 5304 |
| Residence Time | h | 0.41 |
| Loop | | |
| Temperature | ° C. | 75 |
| Pressure | kPa | 5332 |
| Residence Time | h | 0.4 |
| H2/C3-feeding | mol/kmol | 0.25 |
| Split | wt % | 46 |
| MFR | g/10 min | 9.7 |
| First Gas Phase Reactor | | |
| Temperature | ° C. | 85 |
| Pressure | kPa | 2000 |
| H2/C3-Feeding | mol/kmol | 3.3 |
| Split | wt % | 54 |
| MFR | g/10 min | 8.5 |
| Final (H-PP-1) | | |
| MFR | g/10 min | 7.5 |
| TM | ° C. | 153 |
| 2.1 + 3.1 erythro defects | mol % | 0.7 |
| mmmm % | mol % | 98.3 |

2. Preparation of the Polymer Composition (C)

The polymer composition (C) was prepared from the propylene homopolymer (H-PP1) by additivation of the propylene homopolymer H-PP1 with the list of additives as described below. The melt flow rate has been subsequently adjusted with peroxide to the value as indicated below.

The properties of the comparative and inventive composition are found in Table 3.

TABLE 3

Properties of the comparative and inventive composition

| | | HD810MO | H-PP1 |
|---|---|---|---|
| Additives | | | |
| Calcium Steareate | wt % | 0.05 | 0.05 |
| Arenox DL | wt % | 0.21 | 0.21 |
| Irgafos 168 | wt % | 0.15 | 0.15 |
| Primol 352 | wt % | 4.9 | 4.9 |
| Millad 3988 | wt % | 0.15 | 0.15 |
| Final properties | | | |
| MFR | g/10 min | 9.5 | 16.8 |
| Tc | ° C. | 130 | 125 |
| Tm | ° C. | 164 | 155 |
| Hm | J/g | 102 | 97 |
| XCS | wt % | 7.9 | 5.5 |
| Flexural Modulus | MPa | 1201 | 1233 |
| NIS 23° C. | kJ/m$^2$ | 5.5 | 4.5 |
| Haze (1 mm) | % | 17.0 | 17.0 |
| Overall Migration (1 mm) | | 81.9 | 48.0 |

Arenox DL dodecyl 3-{[3-(dodecyloxy)-3-oxopropyl]sulfanyl}propanoate (CAS-no. 123-28-4);, commercially available of BASF
Irgafos 168 is Tris(2,4-tert-butylphenyl) Phosphite commercially available by BASF;
Primol 352 While oil; a purified mixture of liquid saturated hydrocarbons; Kinematic viscosity (40° C.; ASTM D 445) = 65.0-75.0 mm$^2$/s; Dynamic viscosity (20° C.; ASTM D 445) = 165 mPas, commercially available from ExxonMobil;
Millad 3988 is 1.3: 2.4 bis(3,4-dimethylbenzylidene)sorbitol (CAS-no. 135861-56-2), commercially available of Milliken;

Comparative Example CE1 is the commercial polypropylene homopolymer HD810MO (Bormed™ of Borealis AG) is prepared from a Ziegler-Natta catalyst. It has a melt flow rate MFR$_2$ of 10.0 g/10 min, a melting temperature Tm of 164° C., and a density of 907 kg/m$^3$. The polymer chain has a pentad isotacticity (mmmm %) of 96.0 mol % and is free of regiodefects.

3. Overall Migration, Retention of Toughness and Discoloration after Gamma-Ray Sterilization As derivable from the values shown in Table 3, the inventive composition has much lower overall migration than the comparative composition although the mechanical and optical properties of both compositions have been comparable. The mechanical profile have been analysed based on retention of Charpy notched impact strength (% NIS retention) of samples after gammy sterilization and thermal aging. Comparative and inventive samples were prepared from injection moulded specimen having size of 60×60×1 mm$^3$. Samples were sterilized at 50 kGy and aged at 80° C. for 2 months (60 days) before analysis (Table 4). Analysis of discoloration after gamma-ray sterilization has been determined by yellowness index. Samples were sterilized at 50 kGy and aged at 80° C. for 2 months (60 days). Yellowness index of the aged samples was successively determined after ageing at 1, 7, 14, 30 and 60 days (Table 5).

TABLE 4

Retention of toughness after 60 days of aging

|  | CE1 | H-PP1 |
|---|---|---|
| Retention of Charpy notched impact strength (NIS %) | 90 | 88 |

The NIS retention was essentially identical in the comparative and inventive materials.

TABLE 5

Successive discoloration over a period of 60 days of aging

| Yellowness index after n days | CE1* | CE1 | H-PP1* | H-PP1 |
|---|---|---|---|---|
| 1 | 0.2 | 8.0 | 0.0 | 4.9 |
| 7 | 0.2 | 16.3 | 0.1 | 8.1 |
| 14 | 0.2 | 17.3 | 0.0 | 9.2 |
| 30 | 0.2 | 20.2 | 0.2 | 11.7 |
| 60 | 0.3 | 25.1 | 0.2 | 14.6 |

*samples not gamma-ray sterilized;

It was further found that the degree of discoloration of the materials as indicated by yellowness index after gamma-ray sterilization and aging is substantially lower in the inventive material compared to the comparative material.

The invention claimed is:

1. A polymer composition (C), comprising, based on the total weight of the polymer composition (C):
    (a) 91.0 to 98.0 wt.-% of a propylene homopolymer (H-PP),
    (b) 1.98 to 8.98 wt.-% of at least one hydrocarbon oil (WO),
    (c) 0.01 to 0.7 wt.-% of at least one nucleating agent (NA), and
    (d) 0.01 to 2.0 wt.-% of at least one antioxidant (AO);
    wherein the sum of components (a), (b), (c) and (d) adds up to at least 95 wt.-% of the total weight of the polymer composition (C) and the propylene homopolymer (H-PP) is an isotactic propylene homopolymer defined by
    (i) a melt flow rate MFR2 determined according to ISO1133 at 230 ° C. and 2.16 kg in the range from 4.0 to 22.0 g/10 min;
    (ii) a melting temperature in the range of 145 to 162° C. as determined by differential scanning calorimetry (DSC); and
    (iii) a content of 2,1 erythro regio-defects in the range from 0.1 to 1.3 mol % as determined by 13C-NMR spectroscopy.

2. The polymer composition (C) according to claim 1, having a melt flow rate MFR2 determined according to ISO1133 at 230° C. and 2.16 kg in the range from 5.0 to 25.0 g/10 min.

3. The polymer composition (C) according to claim 1, wherein the propylene homopolymer (H-PP) has a polydispersity (Mw/Mn) in the range from 2.0 to 4.5 as determined by GPC according to ISO 16014.

4. The polymer composition (C) according to claim 1, wherein the propylene homopolymer (H-PP) is prepared in the presence of a metallocene catalyst.

5. The polymer composition (C) according to claim 1, wherein the propylene homopolymer (H-PP) is characterized by a high isotacticity, defined as pentad regularity <mmmm> of more than 96.0 mol % as determined by 13C-NMR spectroscopy.

6. A moulded article comprising at least 90 wt. % of the polymer composition (C) as defined in claim 1, based on the total weight of the moulded article.

7. The moulded article according to claim 6 being a medical, pharmaceutical or diagnostic article.

8. The moulded article according to claim 6, which has been gamma-ray sterilized at a dose of at least 15 kGy.

9. The moulded article according to claim 6, having an overall migration in the polymer composition (C) as determined according to EN ISO 1186-14:2002 on injection moulded plaques, 60×60×1 mm$^3$ of less than 60.0 mg/dm$^2$.

10. The moulded article according to claim 6, having a discoloration of the polymer composition (C) after gamma-ray sterilization at 50 kGy and 60 days of aging as defined by yellowness index of not higher than 23 as determined on injection moulded plaques 60×60×1 mm$^3$ according to standard method ASTM E313.

11. The moulded article according to claim 6, having a Charpy notched impact strength in the range of 2.5 to 15.0 kJ/m$^2$, as determined according to ISO 179 1 eA, and a retention of said impact strength after gamma-ray sterilization at 50kGy and 60 days of aging of more than 75%.

12. A process for gamma-ray sterilization of articles comprising the steps of:
    providing the moulded article as defined by claim 6, and
    subjecting said moulded article to gamma-ray sterilization.

13. The process according to claim 12, wherein the gamma-ray sterilization is carried out at a dose in the range of 15 to 150 kGy.

* * * * *